United States Patent [19]
Xu et al.

[11] Patent Number: 5,717,130
[45] Date of Patent: Feb. 10, 1998

[54] METHOD AND APPARATUS FOR DETERMINING EMISSION MEASUREMENT ACCURACY

[75] Inventors: Y. Ron Xu, Vernon Hills; William B. Rush, Antioch, both of Ill.

[73] Assignee: Outboard Marine Corporation, Waukegan, Ill.

[21] Appl. No.: 704,219

[22] Filed: Aug. 23, 1996

[51] Int. Cl.⁶ ................................................. G01N 7/00
[52] U.S. Cl. .................................................. 73/23.31
[58] Field of Search .......................... 73/23.31, 117.3; 340/439

[56] References Cited

U.S. PATENT DOCUMENTS 5,343,906  9/1994  Tibbals, III ........................... 73/23.31

OTHER PUBLICATIONS

SAE Technical Paper Series, pp. 119–127, reprinted from Design, Modeling, and Emission Control for Small Two–and Four–Stroke Engines (SP–1195); "A Convenient Technique for Determining Two–Stroke Emission Measurement Accuracy and A/F Ratio"; Ron Y Xu.

Society of Automotive Engineers; pp. 1–18; "Development of a Fuel–Based Mass Emission Measurement Procedure"; Donald L. Stivender.

*Primary Examiner*—Robert Raevis
*Attorney, Agent, or Firm*—Jones, Day, Reavis & Pogue

[57] ABSTRACT

Methods and apparatus for determining and assessing the accuracy of exhaust gas measurements using the total emission method is provided which allows for virtually real-time determination of the presence of a source of inaccuracy in the total emission measurement, thereby notifying an operator to interrupt the test prior to its completion to search out the source of the inaccuracy. In accordance with one aspect of the present invention, the measured total hydrocarbons are treated as unburned fuel ($C_8$ basis) plus burning zone hydrocarbons ($C_1$ basis).

17 Claims, 6 Drawing Sheets

METHOD AND APPARATUS FOR DETERMINING EMISSION MEASUREMENT ACCURACY

FIELD OF THE INVENTION

The present invention pertains to methods and apparatus for determining the emissions of internal combustion engines and the assessment of the accuracy of such determinations on a virtually real time basis.

BACKGROUND OF THE INVENTION

Governmental regulations setting forth maximum allowable emissions from automobile engines have been implemented in many regions. As automobile engines are almost invariably all four-stroke engines, appropriate methods and apparatus for assessing the emission measurement accuracy of four-stroke engines have been developed. While these methods and apparatus have been found suitable for four-stoke engines, they do not provide accurate results with two-stroke engines. It is anticipated that further governmental emission regulations directed to marine engines, snowmobiles, motorcycles, chain saws and other devices may be implemented in the near future. As such devices typically utilize two-stroke internal combustion engines rather than four-stroke engines, the apparatus and methods which have been developed to date for determining the emission measurement accuracy of four-stroke engines are not sufficiently accurate for use in determining the emission measurement accuracy of such two-stroke engines. Accordingly, an improved apparatus and method for accurately determining the emission measurement accuracy of two-stroke engines is desired.

Also, it is important that the accuracy of emission determinations be regularly checked. That is, even with each of the sensors for sensing the amount of various respective constituents present in the emissions being accurately calibrated, there may be other sources of inaccuracy present which result in inaccurate determinations of emissions. For instance, one commonly employed technique for assessing the accuracy of emissions with current apparatus and methods is referred to as the total, percentage emission technique. Engine exhaust gases consist of $CO$, $CO_2$, $H_2$, $O_2$, $NOx$, $N_2$, $Ar$, $H_2O$ and $HC$. It is apparent that the ideal value of total percentage emissions put out by the engine should be exactly 100% of what was put into the engine (the quantity of fuel and air) if all constituents of the dried exhaust gases are directly measured without error. However, if there exists, for instance, an unknown leak in the passageway from the engine exhaust to the analyzers, or other potential sources of error introduction, additional unburned air may unknowingly be drawn into the passageway and/or exhaust gases escape through the passageway to atmosphere, producing inaccurate results. In accordance with current methods and apparatus for assessing the accuracy of total emission outputs, it is necessary to run a full battery of tests before then going back and manually analyzing the results to determine whether or not the tests which were just run were accurate. There is a need for a method and apparatus for assessing the accuracy of exhaust gas measurements using the total emission method which allows for virtually real time determination of inaccuracies in the total emission measurements so that an operator can be alerted to interrupt the test virtually immediately upon detection of an error, and prior to completion of the test being run, rather than after the test is completed and analyzed, thereby saving considerable time and expense.

SUMMARY OF THE INVENTION

In accordance with the present invention, a method and apparatus for assessing the accuracy of exhaust gas measurements using the total emission method is provided which allows for virtually real time determination of the presence of a source of inaccuracy in the total emission measurement, thereby notifying an operator to interrupt the test prior to its completion to search out the source of the inaccuracy. The accurate determination of hydrocarbon mole percentage in the exhaust gas is important for the total emission method. This invention presents a new method for accurately determining hydrocarbon mole percentage. The measured total hydrocarbons are treated as unburned fuel ($C_8$ basis) plus burning zone hydrocarbons ($C_1$ basis).

Appropriate sensors for detecting the quantity of $CO$, $CO_2$, $O_2$, $NO_x$, and $HC$ present in the exhaust emissions of the internal combustion engine over a selective period of time are employed. Also, an appropriate sensor for detecting the flow rate of fuel supplied to the internal combustion engine over the same selective period of time is employed. This data is fed to a processor which calculates the average quantifies of each of these respective emission components and of the fuel flow rate over the selective period of time. The processor repeatedly calculates the total percentage emission utilizing the averaged data of, $CO_2$, $O_2$, $NO_x$, $HC$ and fuel flow rate. An acceptable accuracy range is either set or calculated. The calculated total percentage emission repeatedly compared to the accuracy range. If one of the calculated emissions falls outside of the acceptable accuracy range, then a warning indicia is actuated, or the system is automatically shut down. This alerts the operator to interrupt the test and search for and correct a source of error in the system before restarting the testing.

DETAILED DESCRIPTION OF THE PREFERRED EMBODIMENTS

Disclosed are methods/and apparatus for assessing the accuracy of total emission measurements on a virtually real-time basis. Also disclosed are methods and apparatus for calculating the air-to-fuel ratio (A/F) of an internal combustion engine, which methods and apparatus are suitable for use with both conventional carbureted and direct injected (DI) two-stroke engines.

Both engine performance and exhaust emissions are important criteria for optimal engine calibration, which will become increasingly important with the implementation of stricter emission regulations. The engine calibration can be performed more accurately and faster if the total percentage emissions and air-to-fuel ratio are computed and shown on a computer screen during the engine calibration. These calculations may also be a part of the computerized calibration programing, in the preferred embodiment. Although this method is developed for two-stroke engines, it is also applicable to four-stroke engines. In addition, this method can be used for both conventional gasoline and oxygenated fuels.

TOTAL EMISSION METHOD AND APPARATUS

The total mole percentage method of exhaust gas analysis is a practical method for assessing the accuracy of emission measurements. This method is also a useful tool to check the accuracy of the air-to-fuel ratio (A/F) calculation because the accuracy of the A/F calculation depends on the emission measurement. The total dry emissions is given by:

$$\text{Total dry emissions } \% = [CO]+[CO_2]+[H_2]+[O_2]+[NOx]+[N_2]+[Ar] +\Sigma[HC] \quad (1)$$

It is apparent that the ideal value of total emissions should be 100% if all constituents of the dried exhaust gases are directly measured without error. Many of these constituents may be directly and precisely measured. CO, $CO_2$ and $O_2$ volumetric percentage concentrations are measured on a dry basis. $NO_x$ is measured on a wet basis which should be converted to the dry basis.

Dry $H_2$ concentration may be calculated from following well-known equation, which is recommend by US EPA NPRM 91-427 and ICOMIA standard, $$[H_2] = \frac{0.5*Y*[CO]*([CO]+CO_2])}{[CO]+(3*[CO_2])} \quad (2)$$

$[N_2]$ and $[Ar]$ can be calculated from the Argon balance and Nitrogen balance, $$[Ar]=0.043(0.5*[CO]+[CO_2]+0.5*[H_2O]+[O_2]+0.5*[NO_x]) \quad (3)$$

$$[N_2]=3.72*(0.5*[CO]+[CO_2]+0.5*[H_2O]+[O_2]+0.5*[NO_x]) \quad (4)$$

It is the inventor's belief that the determination of hydrocarbon (HC) mole percentage in the dried exhaust gases is crucial for accuracy in employment of the total emission method. Previously, the measured total HC concentration ($ppmC_1$) was used to calculate the total percentage emission.

Generally, HC emissions are measured by a HFID (Heated Flame Ionization Detector) analyzer and the level of HC in the exhaust gases is specified in terms of the total hydrocarbon concentration, expressed in part per million carbon atoms ($ppmC_1$). This is because the HFID analyzer is effectively a carbon atom counter. It is theoretically not correct to be using measured total HC concentration ($ppmC_1$), to represent the mole percentage of HC in the dried exhaust gases. This would be correct if all the hydrocarbons in the exhaust gases were only methane ($CH_4$). However, the results of hydrocarbon species analyses for outboards using gasoline fuel, shows that the exhaust gases contain a wide variety of hydrocarbon compounds with carbon numbers from $C_1$ to $C_{12}$. Therefore, using the conventionally-employed assumption that a count of $C_1$ atoms provides a sufficiently accurate estimation of the hydrocarbons in the emission, the which is acceptable for four-stroke engines, total emissions are over-estimated by using the measured total HC concentration ($ppmC_1$) as the mole percentage of HC in two-stroke engines. The assumption does not cause a problem for four-stroke engines because four-stroke engines do not have the problem of short-circuiting unburned fuel, which is realized with two-stroke engines, and four-stroke engines have a relatively lower average HC emission. For the four-stroke engine, the range of HC emissions is about 1000–4000 $ppmC_1$ (0.1–0.4%) and it is negligibly small for its effects on the over-estimation of the total emission calculation.

In two-stroke engines, the combined intake and exhaust process is defined as scavenging. An unavoidable part of the scavenging process is the short circuiting of the fresh fuel and air mixture directly through the cylinder into the exhaust. Short circuiting is obviously undesirable, but inevitable to at least some extent in two-stoke engines, particularly in order to achieve homogeneity of the air-fuel charge at higher engine speeds in two-stroke engines.

Figure 1:
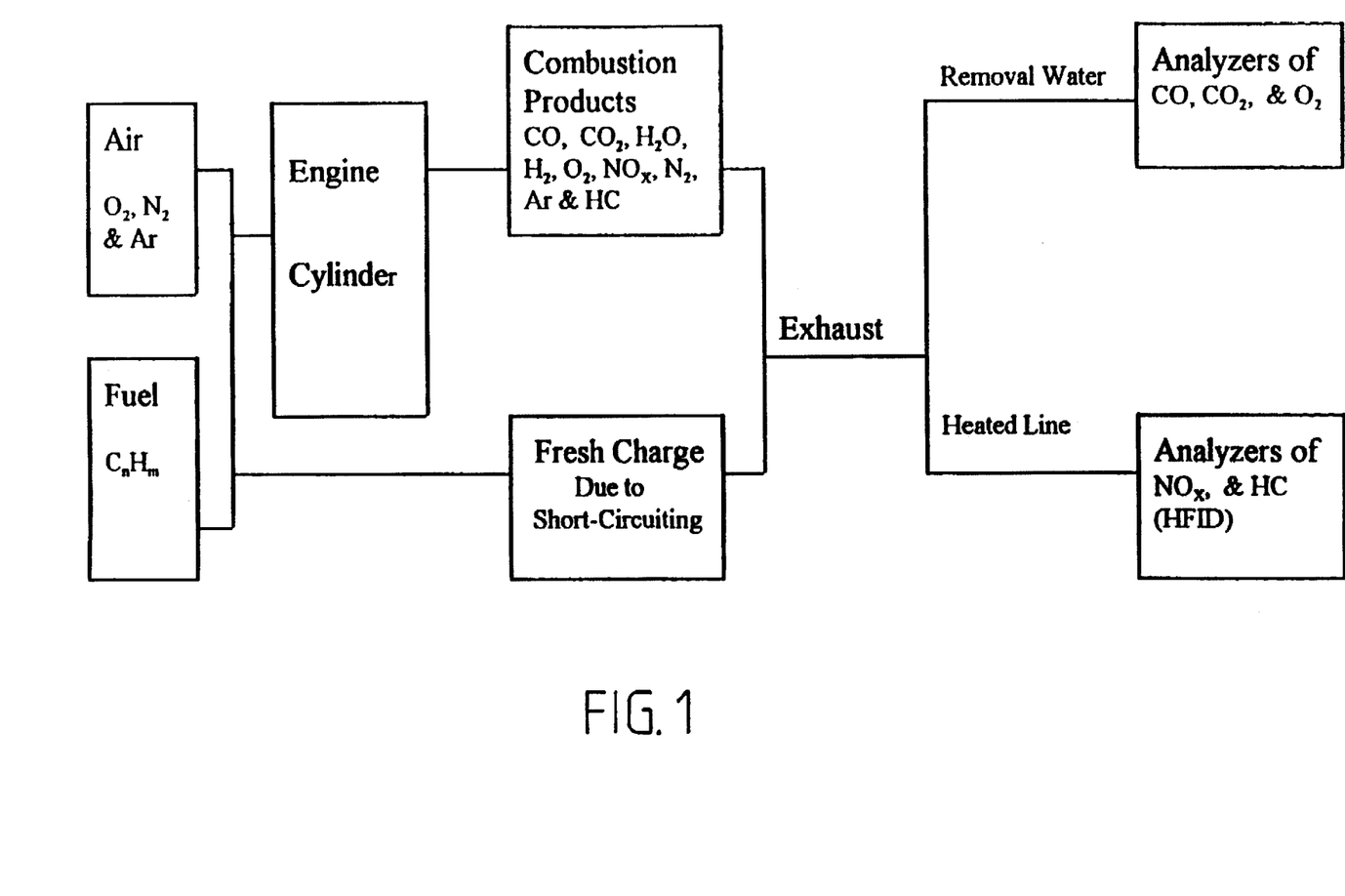
FIG. 1 is a schematic diagram of a scavenging, combustion and emission measurement arrangement for carrying out the present invention.

FIG. 1 shows the flow diagram of scavenging, combustion and emission measurement for two-stroke engines. There are two major differences between conventional two-stroke and four-stroke engines. First, two-stroke engines have very high HC emissions and oxygen concentration in the exhaust due to the short-circuiting, as compared with four-stroke engines. The range of HC emissions for the carbureted two-stroke engines is 20,000–150,000 $ppmC_1$ (2%–15%), which mainly is unburned fuel, but is not on a $C_1$ basis. Second, the measured combustion-generated emissions of CO, $CO_2$, $O_2$, HC and $NO_x$ have been diluted by the fresh air-fuel mixture due to short-circuiting of the fresh air-fuel mixture.

It is obviously desirable, and optimal accuracy may be obtained, by determining the mole percentage of all HC species. However, this is not necessary for assessing the accuracy of the emission measurement by using the total emission method in accordance with the present invention. To avoid the over-estimation of HC mole percentage for two-stroke engines, the method according to the present invention comprises making the assumption that HC in the exhaust gases exists in two forms: partially burned HC (burning zone HC emissions) with $C_1$ basis, $[HC]_{C_1}$; and unburned fuel, $[HC]_{C_nH_m}$. The current gasoline fuels consist of the compounds $C_5$–$C_{11}$. By way of illustrative example, the average value of $C_8$ will be used for this calculation in the preferred embodiment of the invention; however, other hydrocarbons such as $C_7$, $C_9$, etc. could be used in the alternative. Utilizing the above assumption, the mole percentage of HC in the exhaust gases for the total emission calculation may be given as:

$$\Sigma HC=[HC]_{C_1}+[HC]_{C_8}, \% \quad (5)$$

The HC emissions in the burning zone and unburned fuel can be obtained by using the trapping efficiency analysis as follows. The trapping efficiency is defined as:

$$\eta_{tr} = \frac{\text{Fresh charge remaining in cylinder}}{\text{Total aspirated charge}}$$

The simple and common method for the rich mixture (richer than stoichiometry) uses the ratio of exhaust oxygen to 21%, which leads to the equation:

$$\eta_{tr} = 1 - \frac{[O_2]}{21\%} \quad (6)$$

However, this is not very accurate. First, the total aspirated charge includes the air and the fuel; second, the $[O_2]$ is measured dry. A correction factor K should be used to convert dry measurement to a wet basis, which was proposed by US EPA, NPRM 91-427.

Therefore, a more precise determination of trapping efficiency may be written as follows:

$$\eta_{tr} = 1 - \frac{K^*[O_2]}{\frac{\text{Air}}{\text{Fuel}+\text{Air}} *21\%} = 1 - \frac{K^*[O_2]}{\frac{A/F}{1+A/F} *21\%} \quad (7)$$

where A/F is the air to fuel ratio and the equation of A/F is shown in the next section.

After the trapping efficiency has been obtained, the burning zone CO, $CO_2$ and $NO_x$ may be calculated from the measured emission data divided by the calculated trapping efficiency. The burning zone HC, however, is not so simple. The rate of unburned fuel due to short-circuiting can be obtained from the measured fuel flow rate and the calculated trapping efficiency. Therefore, the mole percentage of the burning zone HC and unburned fuel can be given as follows:

$$[HC]_{C_1} = \frac{HC_{ppmC_1}}{10^4} * \left(1 - \frac{Q^*(1-\eta_{tr})}{W_{HC}}\right), (\%) \quad (8)$$

$$[HC]_{C_8} = \frac{HC_{ppmC_1}}{8*10^4} * \frac{Q^*(1-\eta_{tr})}{W_{HC}}, (\%) \quad (9)$$

Where:

Q=Fuel flow rate, [g/hr].

$HC_{ppmC1}$=Measured total HC emission, $ppmC_1$ $W_{HC}$=Average mass flow rate of HC emission [g/hr] which may be calculated by using the EPA equation (NPRM 91-427).

The above two equations (8) and (9) and may be used for both carbureted and direct-injected two-stroke engines, and is suitable for use with all EPA modes. The mixture of air and fuel is non-homogeneous for the direct-injected two-stroke engines. Therefore, for the direct-injected two-stroke engines, the trapping efficiency in the above two may be calculated using the aforementioned equation for fuel trapping efficiency. Generally, the HC emission for a direct-injected two-stroke engine is very low compared with two-stroke carbureted engines.

ASSESSING ACCURACY OF EMISSION MEASUREMENTS

Several engines have been tested by following the established EPA five mode emission test procedures. These engines include four-strokes and two-strokes, in which there are carburetors, carburetor body fuel injection, and direct cylinder injection two-stroke engines. The power range for these engines is 2 HP-250 HP. The engine-out emissions were measured by a PIERBURG AMA 2000 emission bench. All analyzers (CO, $CO_2$, $NO_x$, HC, and $O_2$) were properly calibrated and have an accuracy of better than 1% of full scale.

Figure 2:
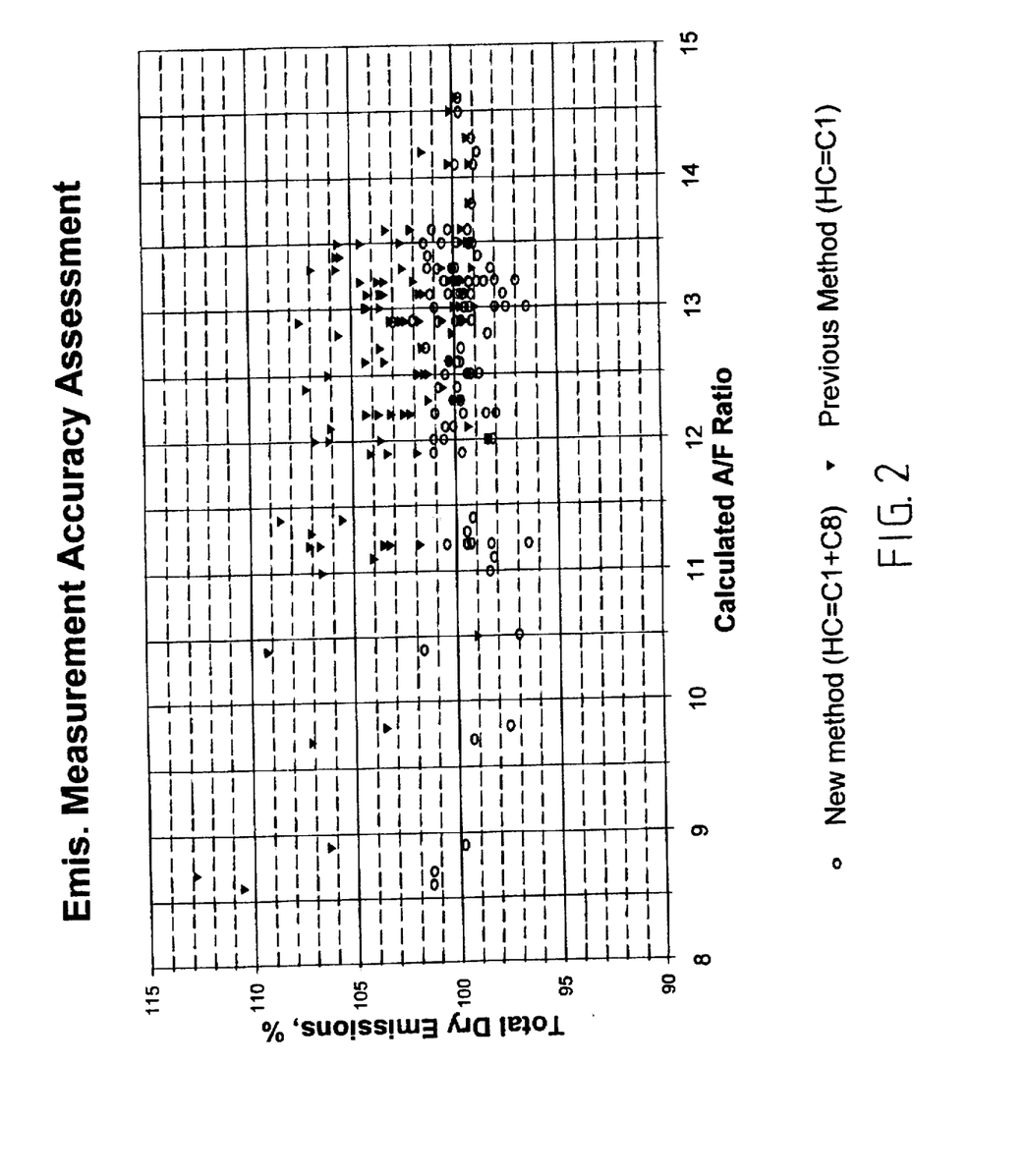
FIG. 2 is a graph comparing the total calculated air-to-fuel ratio of emissions calculated by the prior art method and the method of the present invention.
Figure 3:
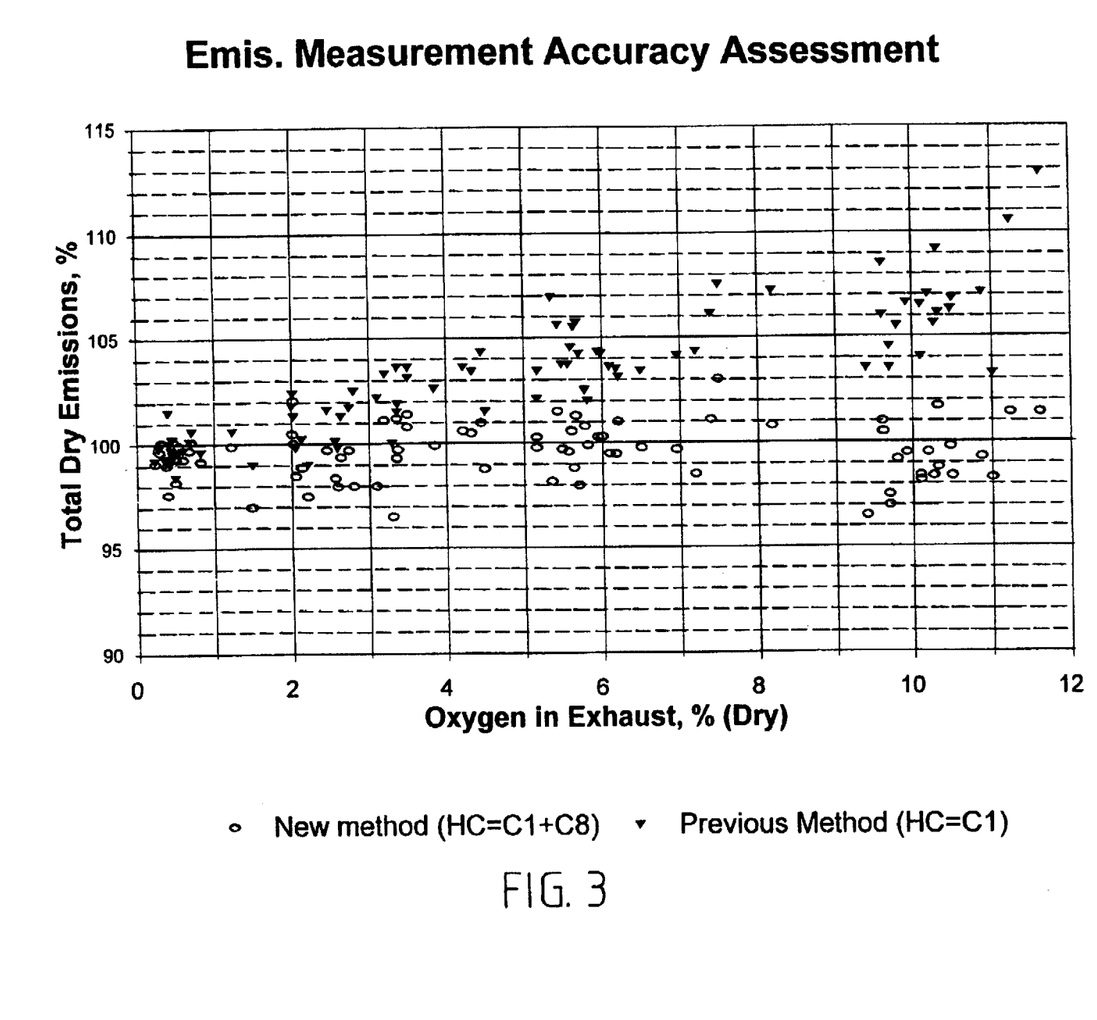
FIG. 3 is a graph illustrating a comparison of the total calculated oxygen ration of the emissions calculated by the prior art method and the method of the present invention.

Both the conventional total emission method and the total emission method of the present invention were used for assessing the accuracy of the emission measurements for the emission tests. FIGS. 2 and 3 show a comparison Of calculated total dry emissions using the two methods. The HC was treated as $C_1$ for the conventional method, and HC was treated as burning zone HC ($C_1$ basis) plus unburned fuel ($C_8$ basis) for the new method. The results of total emission calculation shown in FIG. 3 indicate that it is sufficiently accurate for both methods if the oxygen concentration is less than 3%. However, the total emissions will be over-estimated with the presence of a greater oxygen concentration using the conventional method. It is very difficult to judge if the test data is of poor quality or the total emission quantity is over-estimated during the emission test. Therefore, the previous method, in which HC is treated as total HC emission ($ppmC_1$), is not suitable if the oxygen concentration is more than 3%. However, current emission test data shows that the oxygen concentration will exceed 3% for a large number of current two-stroke engine operating conditions.

Figure 4:
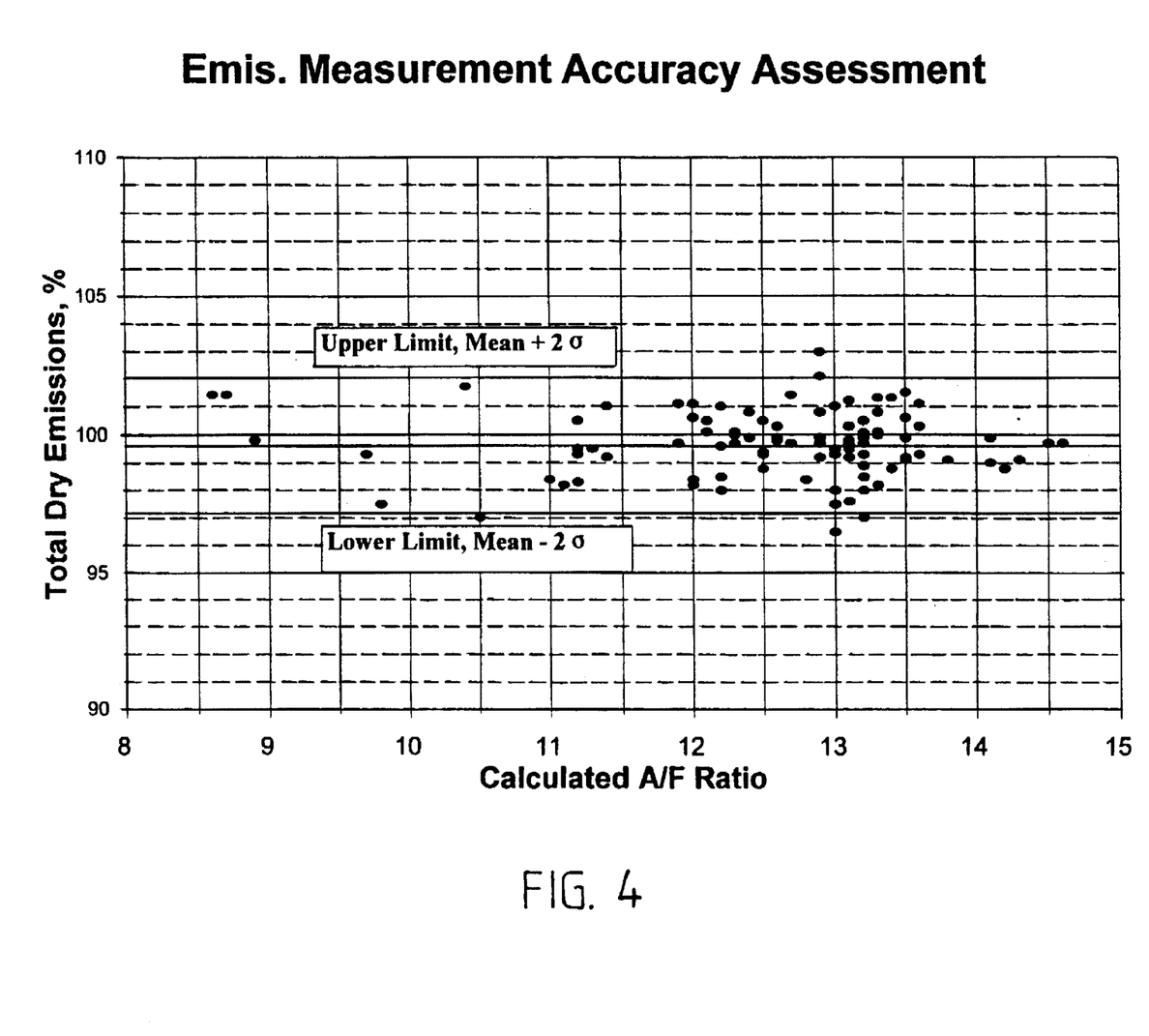
FIG. 4 is a representative graph used for assessing the emission measurement accuracy assessment in accordance with one aspect of the present invention.

The total emission calculation, in which the HC is treated as burning zone HC ($C_1$ basis) plus unburned fuel ($C_8$ basis), has been programmed and shown on a computer monitor during the emission test, although in other embodiments of the invention no visual display is required. FIG. 4 shows an example of using the total emission method to assess the accuracy of an individual emission measurement system. The mean value of total emission calculations is 99.6%, which is a small error caused by un-removed water vapor in the exhaust sample line. It is difficult to completely remove the water vapor in the "cold" sample line and this will cause a lower value of CO, $CO_2$, and $O_2$ measurements, leading to an under-estimation of total emission.

To determine the accuracy of emission test data, an upper and lower limit of total percentage emissions for the emission measurement system, preferably based on statistical analysis, is employed. In accordance with the preferred embodiment of the invention, the emission test will actuate a warning indicia indicating that the test should be stopped if the total emission calculation exceeds $100\pm20\sigma$ during the test. If this occurs, preferably the testing apparatus will have some warning indicia activated, alerting the operators to check the emission measurement system. Otherwise, a repeat emission test may be required by the emission engineer after review of the data, and after all the testing is completed, which wastes considerable time and expense. In accordance with one aspect of the present invention, the emission test data is questionable if the total emission number exceeds the range of $100\pm2\sigma$ (95% confidence level).

Figure 5:
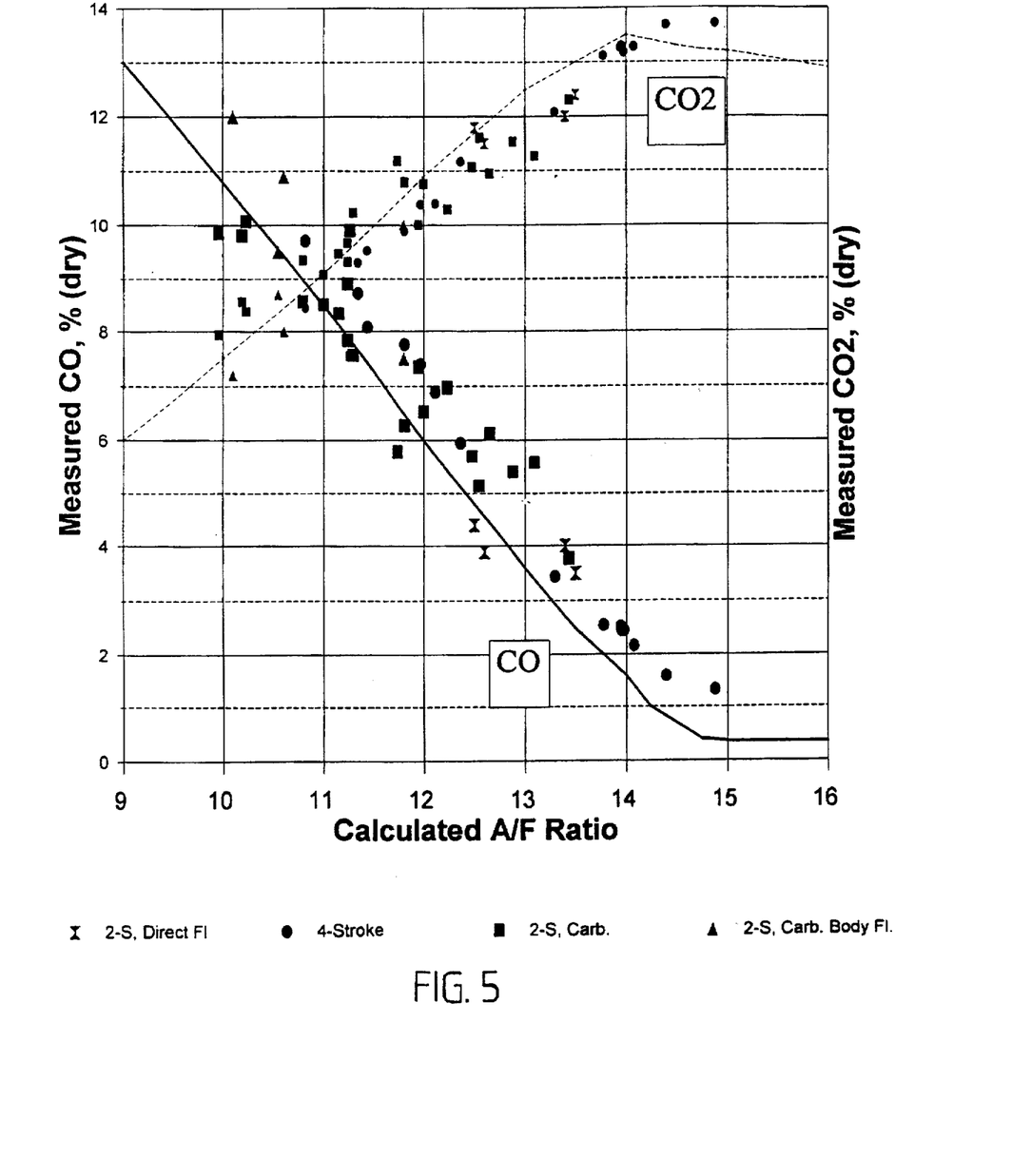
FIG. 5 is a graph illustrating the correlation of measured $CO$ and $CO_2$.

FIG. 5 shows an experimental correlation of CO and $CO_2$, in which the big markers represent the CO data and the small markers are the $CO_2$ data. For the four-stroke engine, the data shown in FIG. 5 is measured CO and $CO_2$. However, the data for the two-stroke engines are the burning zone CO and $CO_2$. It is very interesting that the correlation is suitable for all types of engines which were tested, which includes four-stroke, two-stroke carbureted, carburetor body fuel injection and direct injection engines; This curve provides a useful tool for further trouble shooting. It indicates errors of CO or $CO_2$ measurement if the measured CO or $CO_2$ data deviate from the correlation.

Figure 6:
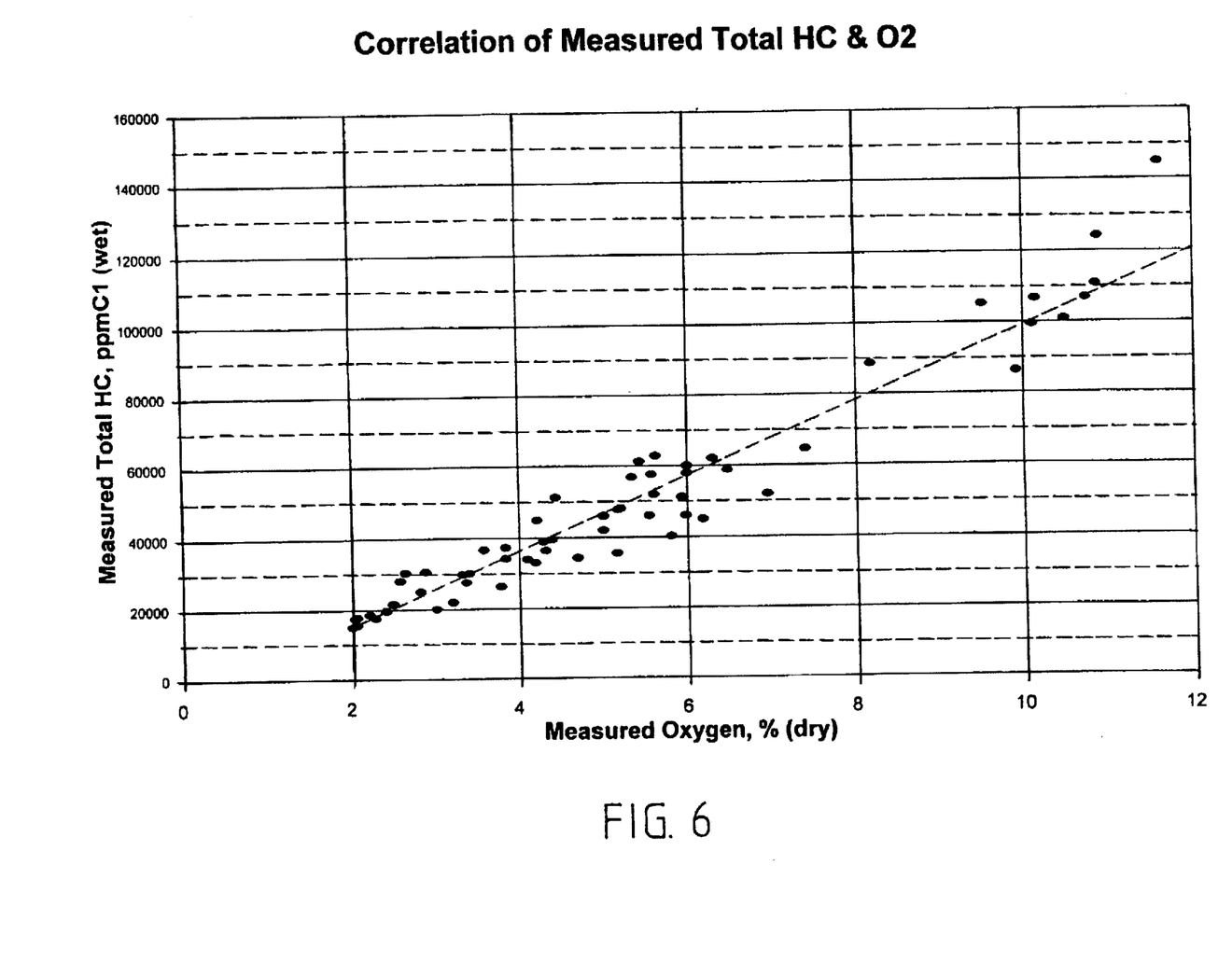
FIG. 6 is a graph illustrating the correlation of measured total $HC$ and $O_2$ for a two-stroke carbureted engine.

An experimental correlation of measured total HC emission and $O_2$ is shown in FIG. 6, which is only suitable for two-stroke carbureted engines. If the measured HC and $O_2$ data deviate from the correlation, there are several possible sources of error. These would include: leakage of the heated sample line, problems with related heated sample line control, a drying problem of a "cold" sample line and, of course, the poor quality data of HC and $O_2$ measurements.

It will be appreciated that, although the invention is described herein in connection with the total mole percentage method of exhaust gas analysis, the methods and apparatus disclosed herein for assessing the accuracy of emission measurements on a virtually real-time basis are applicable to other methods of exhaust gas analysis besides the total mole percentage, or total emission, method.

AIR FUEL RATIO CALCULATIONS

The equation derived from the basic chemical equations for combustion may be used to estimate the air-to-fuel ratio for two-stroke engines.

$$\left(\frac{A}{F}\right) = 4.763 \left(\frac{M_{air}}{M_{fuel}}\right) \frac{\frac{1}{2}[CO] + [CO_2] + \frac{1}{2}[H_2O] + [O_2] + \frac{1}{2}[NO]}{([CO] + [CO_2] + [HC])} \quad (10)$$

where $M_{fuel} = 12.011 + 1.0079*Y$ and $M_{air} = 28.96$.

The following equation may be used to determine the combustion water, $H_2O$:

$$[H_2O] = \frac{0.5*Y*Kc*[CO_2]*([CO]+[CO_2])}{[CO]+Kc*[CO_2]} \quad (11)$$

Where Kc is the water-gas equilibrium constant. In fact, Kc is an empirical constant determined from exhaust composition data and the temperature at which exhaust reactions freeze. It has been suggested that the temperature (reaction freeze) vary from 1666 K to 1810 K and the Kc value is from 3.25 to 3.8. In the preferred and illustrated embodiment, the average value of 3.5 has been selected; however, other values may be employed without deviating from the present invention.

For two-stroke carbureted engines (homogeneous mixture), the value of burning zone air-to-fuel ratio on cylinder air-to-fuel ratio) is the same as the overall value. However, it is different for direct-injected two-stroke engines. The above equation may be employed to calculate the overall air-to-fuel ratio for direct-injected two-stroke engines, and the overall air-to fuel ratio may also be obtained by using the direct air and fuel flow measurement. However, this equation and the direct air and fuel flow measurement cannot be used for assessing the burning zone air-to-fuel ratio. The burning zone air-to-fuel ratio is one of the most important factors to affect the engine performance and emissions for direct-injected two-stroke engines. Therefore, it is important to develop a suitable method for determining the burning zone air-to-fuel ratio (A/F) for direct-injected (DI) two-stroke engines.

BURNING ZONE A/F FOR DI TWO-STROKE ENGINES

Theoretically, the equation (10) for air-to-fuel ratio calculation can be used for calculating the burning zone air-to-fuel ratio for direct-injected two-stroke engines if the measured emissions in equation (10) is replaced by the burning zone emissions. Thus the burning zone A/F equation may be derived as follows:

$$\left(\frac{A}{F}\right)_{bz} = 4.763 \left(\frac{M_{air}}{M_{fuel}}\right) \frac{\frac{1}{2}[CO]_{bz} + [CO_2]_{bz} + \frac{1}{2}[H_2O]_{bz} + [O_2]_{bz} + \frac{1}{2}[NO]_{bz}}{([CO]_{bz} + [CO_2]_{bz} + [HC]_{bz})} \quad (12)$$

The analysis shown in FIG. 1 indicates that the burning zone emissions have been diluted by the fresh mixture due to the aforementioned short-circuiting. Therefore, the burning zone emissions, except $[O_2]_{bz}$, can be obtained from the measured emissions divided by the calculated trapping efficiency.

The burning zone oxygen, $[O_2]_{bz}$, may be estimated from the calculated air trapping efficiency and the measured $O_2$ data. If the direct-injected two-stroke engine is running at a rich mixture (richer than stoichiometry), the value of the burning zone $O_2$ will be very low. When the mixture is lean of stoichiometry, the excess $O_2$ in the cylinder can be estimated from the measured $O_2$ and the calculated air trapping efficiency. The air trapping efficiency for the lean mixture may use the data derived from a rich mixture case at the same engine operating condition.

Thus a complete model to calculate the air-to-fuel ratio (A/F ratio) for a two-stroke engine has been established. The sensitivity of the computed A/F ratio results from error in the measurement of emissions.

A/F CALCULATION FOR ENGINE USING OXYGENATED FUEL

A general formula for the gasoline-oxygenate fuels is represented as $C_nH_mO_r$. It may be simplified as $CH_YO_Z$ if the hydrogen carbon and oxygen carbon atomic ratios are known. In many cases, however, the composition of the fuel may be unknown. The hydrogen/carbon (H/C) and oxygen/carbon (O/C) atomic ratios of the mixture can then be determined by mass percentage as follows:

$$Y = \frac{H}{C} = \frac{\left(\frac{\text{mass \% hydrogen}}{1.0079}\right)}{\left(\frac{\text{mass \% carbon}}{12.011}\right)} = 11.917 * \frac{\%H}{\%C} \quad (13)$$

$$Z = \frac{O}{C} = \frac{\left(\frac{\text{mass \% Oxygen}}{16}\right)}{\left(\frac{\text{mass \% carbon}}{12.011}\right)} = 0.7507 * \frac{\%O}{\%C} \quad (14)$$

Hence the equation of A/F for oxygenated fuel may be derived from oxygen balance, $$\left(\frac{A}{F}\right) = 4.763 \left(\frac{M_{air}}{M_{fuel}}\right) \left(\frac{\frac{1}{2}[CO]_{bz} + [CO_2] + \frac{1}{2}[H_2O] + [O_2] + \frac{1}{2}[NO]}{[CO]+[CO_2]+[HC]} - \frac{Z}{2}\right) \quad (15)$$

where $M_{fuel} = 12.011 + 1.0079*Y + 16*Z$ and $M_{air} = 28.96$.

For a total emission calculation, one can use the same equation. However, [Ar] and [N_2] should be modified as follows:

It will be appreciated to those skilled in the art that multiple apparatus may be employed, with one apparatus sensing the amounts of the various emission constituents and sending electrical signals to another one or more apparatus having processors for receiving the electrical signals and performing the aforementioned calculations and displays. Hence, while various aspects of the present invention have been described by way of illustrated and preferred embodiments, the present invention is not limited to the specific embodiments set forth herein, and it will be readily apparent to those skilled in the art that numerous modifications and variations can be made thereto without departing from the essence and scope of the invention as forth in the accompanying claims.

What is claimed is:

1. A method of assessing the accuracy of determinations of the total emissions from an internal combustion engine, the method comprising:

measuring the volumetric percentages of CO, $CO_2$, $O_2$, $NO_x$, and HC present in the exhaust emissions from the internal combustion engine over a selective period of time;

averaging the respective volumetric percentages for each of said emission constituents over said selective period of time;

measuring the fuel flow rate over said selective period of time;

determining unburned fuel ($C_8$) mole percentage and burning zone HC ($C_1$) mole percentage present in said emissions from said internal combustion engine;

averaging the fuel flow rate over said selective period of time;

repeatedly calculating the total percentage emission utilizing the averaged data of CO, $CO_2$, $O_2$, $NO_x$, HC and the fuel flow rate;

determining an acceptable accuracy range;

comparing each of said repeatedly calculated total percentage emissions to said accuracy range; and automatically actuating a warning indicia upon a calculated total percentage emission falling outside of said accuracy range.

2. The method in accordance with claim 1 in which said step of determining unburned fuel ($C_8$) mole percentage and burning zone HC ($C_1$) mole percentage present in said emissions from said internal combustion engine comprises utilization of the following formulae:

$$[HC]_{C_1} = \frac{HC_{ppmC_1}}{10^4} * \left(1 - \frac{Q^*(1-\eta_{tr})}{W_{HC}}\right), (\%)$$

and $$[HC]_{C_8} = \frac{HC_{ppmC_1}}{8*10^4} * \frac{Q^*(1-\eta_{tr})}{W_{HC}}, (\%)$$

where:

Q=Fuel flow rate, [g/hr];

$HC_{ppmC_1}$=Measured total HC emission, $ppmC_1$; and $W_{HC}$=Average mass flow rate of HC emission, [g/hr], which may be calculated by using the formula:

$$W_{HC} = \frac{G_{fuel}}{[CO]+[CO_2]+[HC_{ppmC_1}]/10^4} * \frac{[HC_{ppmC_1}]}{10^4}$$

3. The method in accordance with claim 1 further comprising interrupting the emission measurement if the calculated total percentage emission exceeds said set accuracy limit.

4. The method in accordance with claim 1 in which the step of calculating the total percentage emission is carried out automatically by one or more processors.

5. The method in accordance with claim 1 in which each of said averaging, calculating and comparing steps is carried out automatically by a processor.

6. The method in accordance with claim 1 in which said accuracy range comprises (100%)±(a predetermined multiple of the standard deviation of all previous total emission calculations).

7. The method in accordance with claim 5 in which said accuracy range comprises (100%)±(two standard deviations of all previous total emission calculations).

8. The method in accordance with claim 1 in which said set accuracy limit is initially preset as 100%±3, and the mean and standard deviation of the total percentage emission are automatically calculated over a predetermined number of said repeatedly calculated total percentage emission determinations, and the accuracy limit is reset upon attainment of said predetermined number as (said mean)±(double said standard deviation).

9. The method in accordance with claim 1 further including automatically actuating said warning indicia upon the mean of the total percentage emission calculations falling outside of the range of 100%±1.

10. A method of assessing the accuracy of determinations of the total emissions from an operating internal combustion engine, the method comprising:

repeatedly measuring the quantity of each of CO, $CO_2$, $O_2$, $NO_x$, and HC present in the exhaust emissions of the internal combustion engine over a selective period of time;

generating electrical signals representative of the respective quantities of each of said CO, $CO_2$, $O_2$, $NO_x$, and HC components measured in said exhaust emissions;

repeatedly measuring the fuel flow rate during said selective period of time;

generating electrical signals representative of the fuel flow rate;

operatively coupling a processor to said electrical signals for receiving said electrical signals;

carrying out pre-programmed calculations on the processor of the averages of each of said respective emission components and fuel flow rate over said selective period of time;

repeatedly calculating the total percentage emission utilizing the averaged data of CO, $CO_2$, $O_2$, $NO_x$, HC and the fuel flow rate;

determining an acceptable accuracy range;

comparing each of said repeatedly calculated total percentage emissions to said accuracy range; and automatically actuating a warning indicia upon a calculated total percentage emission falling outside of said accuracy range.

11. A method in accordance with claim 10 in which the step of determining an acceptable accuracy range comprises repeatedly redefining said accuracy range upon each calculation of the total percentage emission.

12. A method in accordance with claim 11 in which the step of determining an acceptable accuracy range comprises repeatedly calculating the standard deviation of the calculated total percentage emissions and setting the range as 100%±double the calculated standard deviation at that point in time.

13. A method in accordance with claim 10 further comprising automatically interrupting said exhaust component and fuel flow rate measurements upon a calculated total percentage emission falling outside of said accuracy range.

14. An emission testing apparatus for determining the accuracy of emission measurements of the exhaust from an internal combustion engine, the apparatus comprising:

a housing defining a passage for directing the emissions of said internal combustion engine a CO sensor mounted in said housing passage for measuring the mount of CO in the emissions of said internal combustion engine over a selective period of time;

a $CO_2$ sensor mounted in said housing passage for measuring the amount of $CO_2$ in the emissions of said internal combustion engine over said selective period of time;

an $O_2$ sensor mounted in said housing passage for measuring the amount of $O_2$ in the emissions of said internal combustion engine over said selective period of time;

a $NO_x$ sensor mounted in said housing passage for measuring the amount of $NO_x$ in the emissions of said interval combustion engine over said selective period of time;

a HC sensor mounted in said housing passage for measuring the amount of HC in the emissions of said internal combustion engine over said selective period of time;

a fuel flow rate sensor operatively connectable to said internal combustion engine for measuring the mount of fuel supplied to said internal combustion engine over said selective period of time;

means for transmitting electrical data representative of the measured amounts of CO, $CO_2$, $O_2$, $NO_x$, HC, and fuel flow rate;

a warning indicia attached to said housing;

an electronic processor, said processor comprising:

means for receiving said data representative of the measured amounts of CO, $CO_2$, $NO_x$, HC, and fuel flow rate;

means for calculating the averages of the respective amounts of CO, $CO_2$, $O_2$, $NO_x$, hydrocarbons, and fuel flow rate over said selective period of time;

means for repeatedly calculating the total percentage emission utilizing the averaged data of CO, $CO_2$, $O_2$, $NO_x$, hydrocarbons and the fuel flow rate;

means for calculating a predetermined acceptable accuracy range for said calculated total percentage emissions;

means for comparing each of said repeatedly calculated total percentage emissions to said calculated accuracy range; and means for automatically actuating said warning indicia upon one of said calculated total percentage emissions falling outside of said calculated acceptable accuracy range.

15. An emission testing apparatus in accordance with claim 14 in which said means for repeatedly calculating the total percentage emission utilizing the averaged data of CO, $CO_2$, $O_2$, $NO_x$, hydrocarbons and the fuel flow rate comprises utilization of the following formulae for determining the amount of hydrocarbons:

$$\text{totalhydrocarbons} = \frac{HC_{ppmC_1}}{10^4} * \left(1 - \frac{Q*(1-\eta_{tr})}{W_{HC}}\right) + \frac{HC_{ppmC_1}}{8*10^4} * \frac{Q*(1-\eta_{tr})}{W_{HC}}$$

where

Q=Fuel flow rate,[g/hr];

$HC_{ppmC_1}$=Measured total HC emission, $ppmC_1$; and $W_{HC}$=Average mass flow rate of HC emission, [g/hr], which may be calculated by using the formula:

$$W_{HC} = \frac{G_{fuel}}{[CO]+[CO_2]+[HC_{ppmC_1}]/10^4} * \frac{[HC_{ppmC_1}]}{10^4}$$

16. An apparatus in accordance with claim 14 in which said means for calculating a predetermined acceptable accuracy range comprises repeatedly calculating the standard deviation of the calculated total percentage emissions and setting the range as 100%±double the calculated standard deviation at that point in time.

17. An apparatus in accordance with claim 14 in which the apparatus further comprises a video screen operatively coupled to said electronic processor, and said electronic processor further comprises means for effecting a visual display of the calculated total emissions and the calculated acceptable accuracy range on said video screen.

* * * * *